United States Patent
Spork et al.

(10) Patent No.: US 10,350,369 B2
(45) Date of Patent: Jul. 16, 2019

(54) SHIELDING MECHANISM FOR AN INJECTION APPARATUS

(71) Applicant: Novo Nordisk A/S, Bagsvaerd (DK)

(72) Inventors: Emil Gram Spork, Copenhagen N (DK); Henrik Bengtsson, Taastrup (DK); Christian Hoejris Nielsen, Copenhagen NV (DK)

(73) Assignee: Novo Nordisk A/S, Bagsvaerd (DK)

( * ) Notice: Subject to any disclaimer, the term of this patent is extended or adjusted under 35 U.S.C. 154(b) by 358 days.

(21) Appl. No.: 15/108,887

(22) PCT Filed: Dec. 16, 2014

(86) PCT No.: PCT/EP2014/078049
§ 371 (c)(1),
(2) Date: Jun. 29, 2016

(87) PCT Pub. No.: WO2015/101487
PCT Pub. Date: Jul. 9, 2015

(65) Prior Publication Data
US 2016/0325052 A1    Nov. 10, 2016

(30) Foreign Application Priority Data

Jan. 6, 2014  (EP) .................................. 14150216

(51) Int. Cl.
*A61M 5/32*    (2006.01)
*A61M 5/00*    (2006.01)
(Continued)

(52) U.S. Cl.
CPC .......... *A61M 5/3234* (2013.01); *A61M 5/001* (2013.01); *A61M 5/2033* (2013.01);
(Continued)

(58) Field of Classification Search
CPC .............. A61M 5/3234; A61M 5/3245; A61M 5/2033; A61M 5/001; A61M 5/3202; A61M 5/24; A61M 2005/3267; A61M 2005/3247

See application file for complete search history.

(56) References Cited

U.S. PATENT DOCUMENTS 4,392,859 A * 7/1983 Dent ..................... A61M 5/326
                                                                    604/198
4,935,013 A   6/1990 Haber et al.
(Continued)

FOREIGN PATENT DOCUMENTS

EP          1949929 A1      7/2008
JP       2005323848 A      11/2005
(Continued)

*Primary Examiner* — Lauren P Farrar
(74) *Attorney, Agent, or Firm* — Wesley Nicolas (57) ABSTRACT

The present invention relates to an injection apparatus for injecting a pharmaceutical liquid drug into the skin of a user. The injection apparatus can be in form of an injection device carrying a needle cannula or in the shape of a needle assembly (10) attachable to an injection device. The outer shell of the injection apparatus is a protective shield (10) divided into different segments (10*a*, 10*b*). These segments are preferably spaced from each other in the longitudinal direction to move individually in the axial direction. Further, the segments are provided with tilting means (14, 15) which are activated to move neighboring segments (10*a*, 10*b*) apart upon relative axial movement of one or more segments (10*a*, 10*b*) whenever an uneven force is applied to the distal end of the shield.

13 Claims, 5 Drawing Sheets

(51) Int. Cl.
*A61M 5/24* (2006.01)
*A61M 5/20* (2006.01)

(52) U.S. Cl.
CPC ............ *A61M 5/24* (2013.01); *A61M 5/3202* (2013.01); *A61M 5/3245* (2013.01); *A61M 2005/3247* (2013.01); *A61M 2005/3267* (2013.01)

(56) References Cited

U.S. PATENT DOCUMENTS

| | | |
|---|---|---|
| 5,167,640 A | 12/1992 | Balding |
| 5,295,965 A | 3/1994 | Wilmot |
| 5,342,320 A | 8/1994 | Cameron |
| 5,591,133 A | 1/1997 | Feuerborn et al. |
| 5,713,872 A | 2/1998 | Feuerborn et al. |
| 5,976,111 A | 11/1999 | Hart |
| 2005/0096599 A1 | 5/2005 | Crawford et al. |
| 2013/0296797 A1* | 11/2013 | Liversidge ............ A61M 5/326 604/198 |

FOREIGN PATENT DOCUMENTS

| | | |
|---|---|---|
| WO | 9301851 A1 | 2/1993 |
| WO | 03/045480 | 7/2003 |
| WO | 2004000397 A1 | 12/2003 |
| WO | 2008/077706 A1 | 7/2008 |
| WO | 2009102612 A1 | 8/2009 |
| WO | 2010147552 A1 | 12/2010 |

* cited by examiner

SHIELDING MECHANISM FOR AN INJECTION APPARATUS

CROSS-REFERENCE TO RELATED APPLICATIONS

This application is a 35 U.S.C. § 371 National Stage application of International Application PCT/EP2014/078049 (published as WO2015/101487), filed Dec. 16, 2014, which claims priority to European Patent Application 14150216.1, filed Jan. 6, 2014.

THE TECHNICAL FIELD OF THE INVENTION

The invention relates to an injection apparatus which can be in the form of a needle assembly attachable to an injection device or in the form of an injection device having a needle cannula attached. The invention especially relates to a protective shielding mechanism shielding at least the tip of a needle cannula during use and especially between injections.

DESCRIPTION OF RELATED ART

Shielded injection needle assemblies are widely known, e.g. from WO 2003/045480 and WO 2008/077706. Such shielded injection needle assemblies are commonly referred to as safety needles since they minimize the risk of being accidentally injured by the sharp end of the needle cannula.

The shielded needle assembly disclosed in WO 2008/077706 is provided with locking means which locks the axial movement of the shield when the needle assembly is no longer mounted on an injection device. However, once the needle assembly is mounted, the shield is free to move when a force is applied to the shield disregarding how the force is applied. If a user e.g. drops the injection device with the needle assembly mounted thereon e.g. onto the floor or a similar hard surface, the impact will press the shield in the proximal direction. This could expose the distal part of the needle cannula which could then be bended or even break.

Shielding systems which has the ability to tilt and thus prevent further use is disclosed in WO 2004/000397, U.S. Pat. No. 5,295,965 and US 2005/0096599. However, these solutions also have the problem that should the user drop the unused injection device onto a hard surface such as a floor or the like, the shield can retract and the tip of the needle cannula can be damaged.

DESCRIPTION OF THE INVENTION

It is an object of the present invention to provide an injection apparatus having enhanced protection against damaged of the tip of the needle cannula should the user drop the injection apparatus or somehow accidentally exposed the front end of the protective shield to an uneven distributed force.

The injection apparatus is thus preferably constructed such that the protective shield is only able to move in the proximal direction when the force applied is evenly distributed to the front end of the shield The invention is defined in the claims. Accordingly, in a first aspect the present invention relates to an injection apparatus comprising the following constructional details:
  a housing,
  a needle cannula having an internal lumen stretching along a longitudinal axis and wherein at least a distal tip of the needle cannula is sharp, and
  a protective shield which is slidable in relation to the housing between a first position and a second position; the first position being a position in which the tip of the needle cannula is covered by the shield, and
  the second position being a position in which the tip of the needle cannula is exposed to perform an injection.

The protective shield is formed from a number of separate segments which individually is able to slide in the axial direction. The individual segments are thus spaced apart in the longitudinal direction and provided with tilting means that forces neighbouring segments in a radial direction upon axial movement of at least one of the individual segments.

The individual segment of the shield that is first to contact the floor should the injection apparatus be dropped onto a floor, thus slides axially upon impact with the floor. This relative axial movement of the segments forces one of the neighbouring segments to move radially. During this combined axial and radial movement at least one of the segments will get jammed and thus prevent further movement.

The mechanism that jams the relative movable segments can be realized in many different ways. A preferred way is to have a narrow guiding passage for the shield such that the radial movement of the segments would press against the narrow passage. In a preferred embodiment, the passage can be provided with stopping means e.g. realized as ribs.

The individual segments are thus provided with means which would make the individual segments tilt should the force be unevenly distributed. Once the segments tilts, the segments will jam and thus prevent further movement. It is thus accomplished that once neighbouring segments slides relatively to each other the individual segments work together in a way blocking all the segments from sliding further.

The means transforming the axial movement of the neighboring segments in relation to each other to a radial movement of at least one of the neighboring segments is preferably made up from a first element provided on a first neighboring segment and a second element provided on a second neighboring segment.

Whenever the first segment and the second segment engages as the neighboring segments slides axially, the first element and the second element are shaped such that the neighboring first and second segments are forced to move apart from each other in a radial direction.

By engage means broadly that the first element and the second element encounters each other by being brought into physical contact. The wording engage thus encompasses all ways the two element can abut or otherwise physically obtain contact to each other. The engagement or abutment is preferably releasable such that the segments slides back into their respective initiate positions when the uneven force is removed.

During the relative axial sliding, the tilting means works in a radial direction such that the shield parts move radially when slided axially in relation to each other. In that respect, when the injection apparatus is dropped on a floor or any other surface, the impact generates a force which is uneven distributed which again makes the individual and relatively axially sliding segments jam.

The radial working tilting mans are preferably a number of sloping surfaces which act against each other. In a preferred example the sloping surfaces are formed as a tongue and groove interface having sloping walls such that the individual parts are forced to move radially in relation to each other when moved axially in relation to each other.

In order to maintain neighboring segments in an axial sliding relation, the neighboring segments are preferably provided with coupling means which couples neighboring segments together in the radial direction but allow the neighboring segment to slide relatively in the axial direction.

These coupling or engagement means are preferably formed as a longitudinal groove in one segment and a tail in the neighboring segment.

The tail is preferably T-shaped or dove-tail shaped and the groove is undercut such that the two parts can slide axially but not move apart in the radial direction.

In a further aspect, the housing could be provided with guiding means for guiding the shield. These guiding means at the same time form locking means preventing the shield parts from moving axially when the shield parts are pressed radially away from each other.

In a preferred embodiment, the tilting means are provided proximally on the segments and once the individual segments are pressed radially apart one or more of the segments engage one or more ribs provided internally in the housing. These ribs also form part of the guiding means. To facilitate the abutment with the proximal end surface of the shield part the ribs in the housing can be provided with a steep flange.

The injection apparatus could in one example be an injection device e.g. a pen shaped injection device carrying a needle cannula. However in another example, the injection apparatus could be a needle assembly which is attachable to an injection device. Further, the injection apparatus could be provided with a cleaning chamber as disclosed in international patent application No. PCT/EP2014/071746. As disclosed in international patent application No. PCT/EP2014/071746, this cleaning chamber can in one embodiment have a variable volume. Once the cleaning chamber is filled it could still have a flexible volume, e.g. by having resilient walls which could further be spring operated.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENTS

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula used to penetrate the skin of the user whereas the term "proximal end" is meant to refer to the opposite end pointing away from the user during injection.

FIGS. 1 to 6 disclose a first embodiment. The housing 1 can either be a housing 1 of an injection needle assembly or it can be the housing of an injection device.

Figures 1, 2:
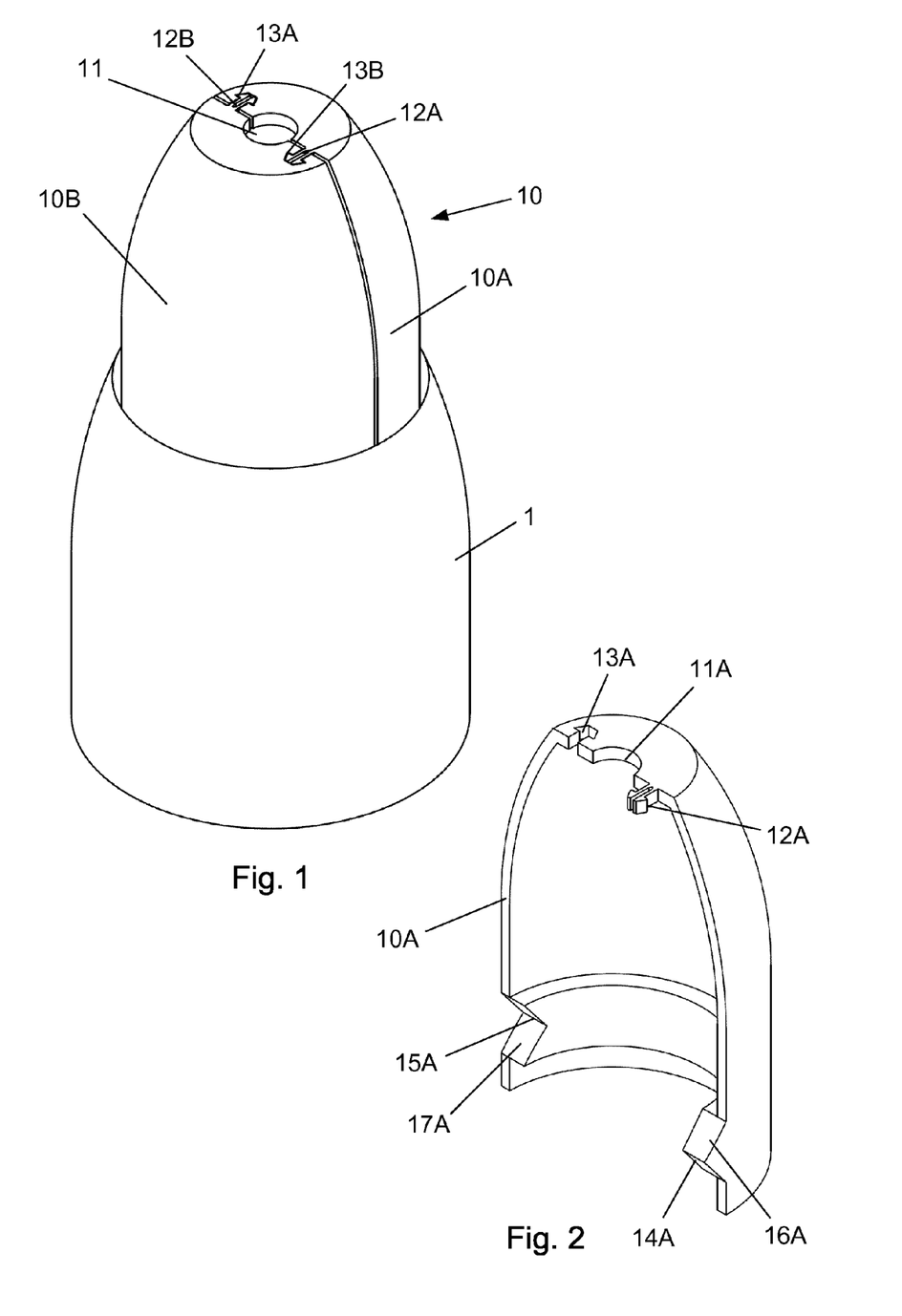
FIG. 1 show a perspective view of an injection apparatus according to the invention.
FIG. 2 show a perspective view of a shield part.

As disclosed in FIG. 1, this housing 1 is provided with a protective shield 10 which is able to telescope in relation to the housing 1 to protect the needle cannula 20. The protective shield 10 telescopes along the longitudinal direction of the injection apparatus, which longitudinal direction is indicted by the broken line "X".

Figure 3:
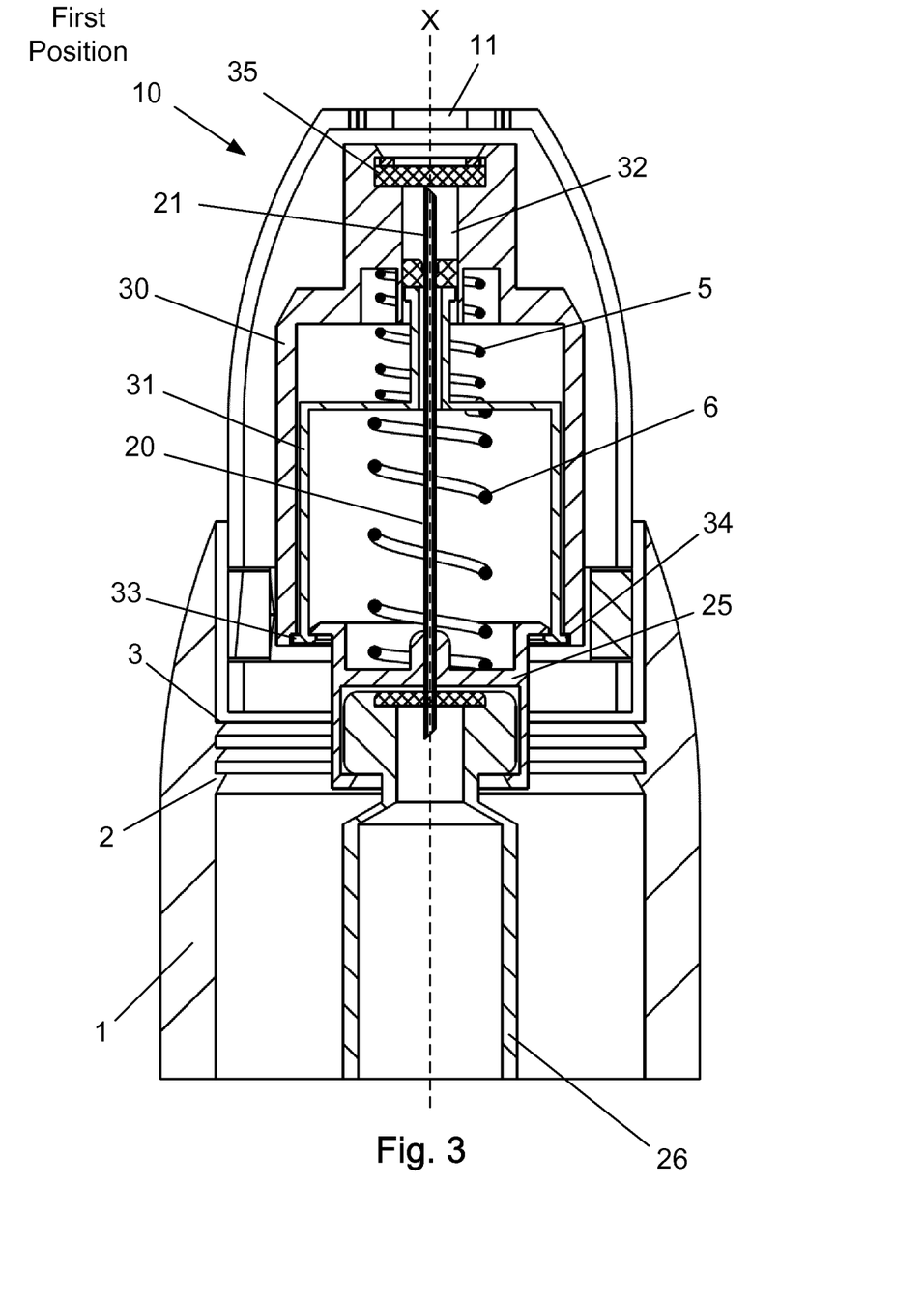
FIG. 3 show a cross sectional view of the injection apparatus in the first position.
Figure 4:
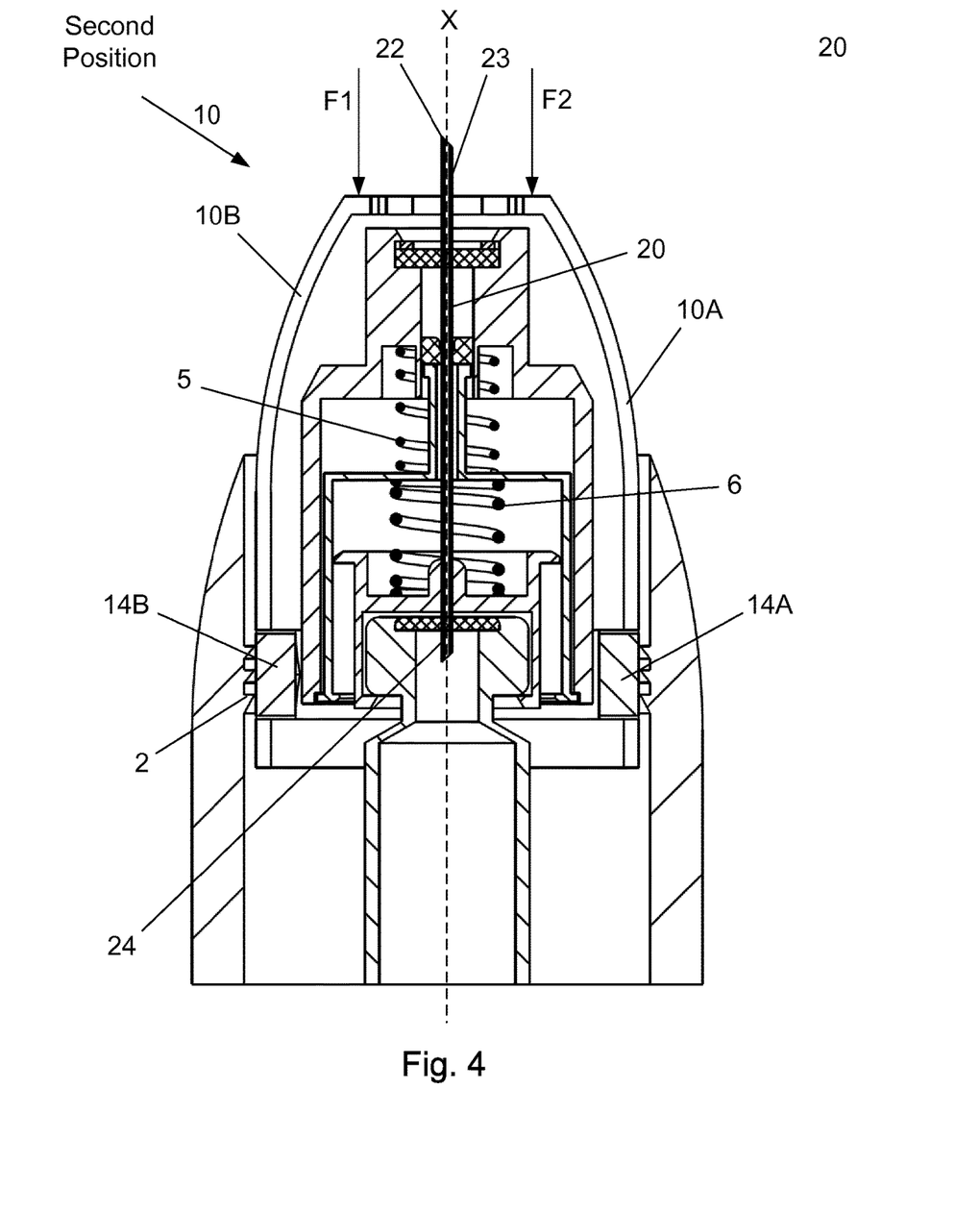
FIG. 4 show a cross sectional view of the injection apparatus in the second position.

In a first position depicted in FIG. 3, the shield 10 covers the distal part 23 of the needle cannula 20 and in the second position depicted in FIG. 4, the shield 10 is retracted such that the distal part 23 of the needle cannula 20 is exposed to perform an injection.

As disclosed in FIG. 1 the housing 1 is in this example shown with the telescopic shield 10 divided into two segments 10A, 10B, however any number of segments 10A, 10B can be provided.

Elements relating to the individual segments 10A, 10B are hereafter numbered by the same reference numbers and prefixed with an "A" or a "B". "A" refer to the first segment 10A, and "B" refer to the second segment 10B.

In the disclosed embodiment, the two segments 10A, 10B are neighbouring each other. However, should more than two segments 10A, 10B be utilized, each will neighbour the neighbouring segments 10A, 10B on either side as the neighbouring segments 10A, 10B are spaced apart in the longitudinal direction X.

The two disclosed segments 10A, 10B together form an opening 11 through which the needle cannula 20 can move during injection. The terminology used to explain that the protective shield 10 cover the distal part of the needle cannula 20 therefore only means that the distal part 23 of the needle cannula 20 is covered when viewed from the side, the distal part 23 of the needle cannula 20 is obviously able to move through the opening 11 in the shield 10 during injection.

The injection mechanism is described in details in international patent application No. PCT/EP2014/071746, and works as follows.

FIG. 3 discloses the injection apparatus with the shield 10 in the first position i.e. between injections. The needle cannula 20 is mounted in a hub 25 which is secured to the cartridge 26 such that the lumen 21 of the needle cannula 20 is in liquid communication with the liquid drug contained inside the cartridge 26.

The needle cannula 20 is mounted such in the hub 25 that a distal part 23 protrudes in the distal direction and a proximal part 24 protrudes in the proximal direction and into the cartridge 26. The tip 22 of the needle cannula 20 is provided distally on the distal part 23 and the outer ends of the needle cannula 20 is connected via the lumen 21 stretching along the longitudinal direction X of the injection apparatus.

Connected to the hub 25 is two chamber parts 30, 31 which in the depicted state are attached to each other and move together in the axial direction.

Together these two chamber parts 30, 31 forms a cleaning chamber 32 containing an amount of the liquid drug. However, this cleaning chamber 32 can be realized in many other ways.

When delivered to a user the second chamber part 31 is located in a distal position inside the first chamber part 30 such that the chamber 32 does in fact not exist. The user then releases the first spring 5 to move the second chamber part 31 in a proximal direction thus generating the chamber 32 and automatically sucking liquid drug from the cartridge 26 through the lumen 21 of the needle cannula 20 and into the chamber 32. Once the second chamber part 31 has reached its proximal position and the chamber 32 is filed, the second part 31 automatically locks to the first chamber part 30 as indicated by the ridge 33 in the second chamber part 32 engaging the track 34 in the first chamber part 30.

The tip 22 of the needle cannula 20 is hereafter maintained inside the liquid drug contained in the cleaning chamber 32 between injections and is thus cleaned by the preservatives of the liquid drug.

FIG. 3 thus discloses the injection apparatus ready to perform an injection i.e. the protective shield 10 is in the first position and the tip 22 of the needle cannula 20 is located inside the cleaning chamber 32.

When injecting as disclosed in FIG. 4, which illustrates the injection apparatus with the protective shield 10 in the second position, the distal surface of the shield 10 is pressed against the skin of the user. This is illustrated by the arrows F1 and F2 in FIG. 4. These forces F1, F2 also presses back the first chamber part 30 and the second chamber part 31 such that the distal end 23 of the needle cannula 20 penetrates through the distal septum 35 provided at the distal end of the chamber 32.

Once the injection has been given, either manually by pressing home an extended tube or automatically by an electric- or spring motor, the user removes the telescopic shield 10 from the skin where after the second spring 6 urges the telescopic shield 10 and both the first chamber part 30 and the second chamber part 31 distally such that the tip 22 of the needle cannula 20 re-enters into the chamber 32 where it is maintained until the next injection.

The housing 1 is further provided with a number of ribs 2 which ribs 2 distally is provided with a steep flange 3. When the pressure F1, F2 is equally applied to the distal end of the shield 10 the ribs 2 support the side wall of the shield 10 as it moves axially.

FIG. 2 depicts the first segments 10A. This segment 10A is distally provided with a half opening 11A which together with a similar half opening provided in the second segment 10B makes up the full opening 11 through which the needle cannula 20 moves during injection. If more than two segments 10A, 10B are utilized, the opening 11 is preferably circular divided into the number of individual segments 10A, 10B to form one full circular opening 11.

The distal end of the first segment 10A is further provided with a radial protrusion or tail 12A which engages a similar groove 13B provided in the second segment 10B. The tail 12A would preferably be formed as a T or as a dove-tail. The groove 13 stretching through the material of the shield 10 in the longitudinal direction X would usable be formed with an undercut to correspond with the T- or dove-tail shape of the tail 12. The purpose of this is to make the neighbouring segments 10A, 10B able to move relatively to its other in the axial direction i.e. in the longitudinal direction X, while not being able to separate in the radial direction The distal ends of the two segments 10A, 10B are in this way coupled together radially but able to slide independently of each other in the axial direction.

The shield 10 is further provided with tilting means 14, 15 which are able to transform relative axial movement of neighboring segments 10A, 10B into radial movement of at least one of the neighboring segments 10A, 10B.

In one example, the first segment 10A is provided with a radial tongue 14A and a radial groove 15A which both engage with a similar groove 15B and tongue 14B provided in the neighbouring segment 10B. Whenever one of these neighbouring segments 10A, 10B are moved axially in relation to the other, the tongue 14A, 14B and groove 15A, 15B arrangement operates as a tilting mechanism thus moving the neighbouring segment 10A, 10B radially apart.

The tongue 14 preferably has a pair of sloping walls 16 engaging similar sloping walls 17 of the groove 15 of the neighbouring segment 10A, 10B such that these sloping surfaces 16, 17 presses the neighbouring segments 10A, 10B apart in the radial direction.

FIG. 2 discloses the tongue 14A with the sloping surface 16A and the groove 15A with the sloping surface 17A. When two neighbouring segments 10A, 10B are used, the sloping surface 16A of the tongue 14A engages the sloping surface 17B of the groove 15B of the neighbouring segment 10A, 10B and vice versa.

Figure 5:
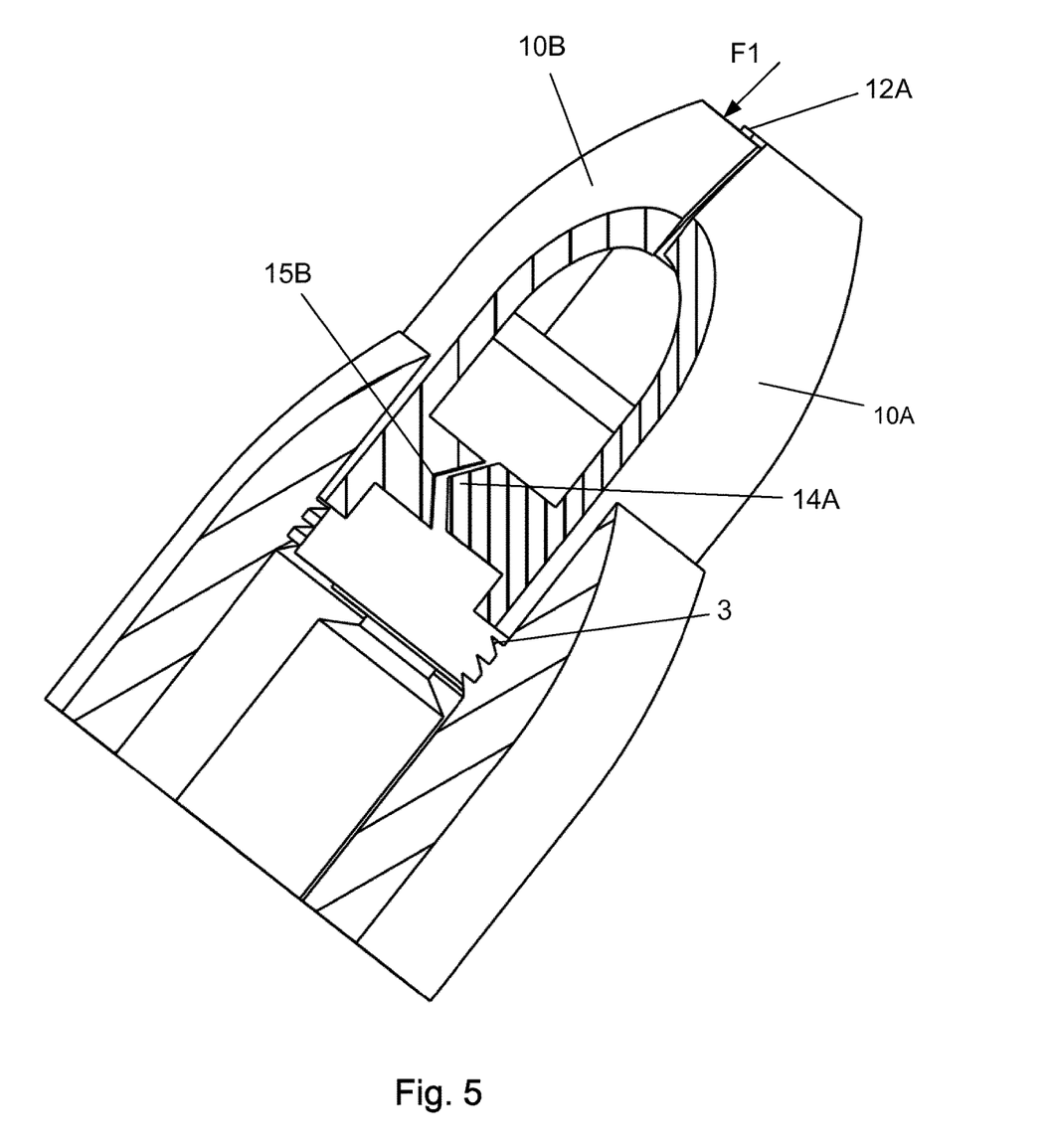
FIG. 5 show a cut-open view of the injection apparatus with the shield parts tilted.
Figures 6, 7:
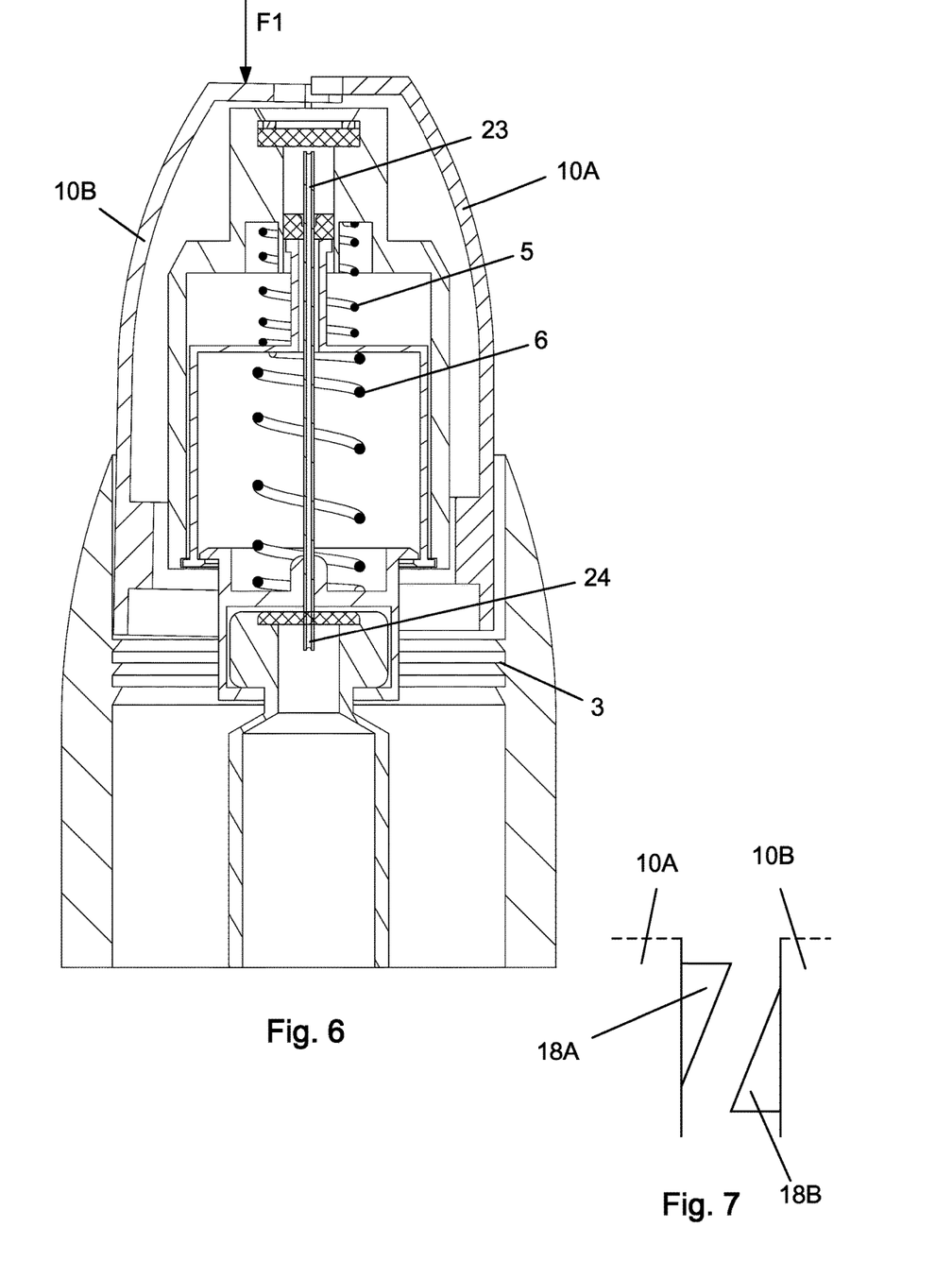
FIG. 6 show a cross section view of the injection apparatus with the shield parts tilted.
FIG. 7 show a partial view of a different embodiment.

If a user drops the injection apparatus onto the floor such that only one of the neighbouring segments 10A, 10B are exposed to a force F1, this would move one of the neighbouring segments 10A, 10B in the proximal direction. In FIG. 5 and FIG. 6, the second segment 10B is moved axially by the force F1. The engagement between the radial tongues 14A, 14B and the grooves 15A, 15B would then cause the neighbouring segments 10A, 10B to deflect radially. The result would be that the proximal end of one of the neighbouring segments 10A, 10B would engage with the steep flange 3 of the rib 2 and thus prevent both segments 10A, 10B from moving further axially.

In the depicted embodiment in FIG. 5, the second segment 10B is moved radially to engage with the flange 3 thus preventing further axial movement of the shield 10 as a whole. The tip 22 of the needle cannula 20 is thereby prevented from being damaged should the user accidentally drop the injection apparatus onto the floor or any other surface.

An alternative embodiment is indicated in FIG. 7. Here each of the two segments 10A, 10B are provided with a protrusion 18A, 18B which is provided in different axial locations. Whenever the neighbouring segments 10A, 10B slides relative to each other, the protrusions 18A, 18B will engage and thus move the neighbouring segments 10A, 10B apart in the radial direction. The protrusions 18A, 18B are disclosed as being triangular but could have any suitable shape, e.g. round, as long as they move the neighbouring segments 10A, 10B radially when sliding axially in relation to each other.

Some preferred embodiments have been shown in the foregoing, but it should be stressed that the invention is not limited to these, but may be embodied in other ways within the subject matter defined in the following claims.

The invention claimed is:

1. An injection apparatus, comprising:
   a housing,
   a needle cannula having a lumen along a longitudinal axis (X) and distal tip, and
   a protective shield which is telescopically slidable in relation to the housing between a first position and a second position;
      the first position being a position in which the tip of the needle cannula is covered by the protective shield, and
      the second position being a position in which the tip of the needle cannula is exposed to perform an injection,
   and wherein the protective shield comprises a plurality of separate segments which segments are radially spaced from each other along the longitudinal direction (X) such that each segment individually and axially slidable both in relation to the housing and in relation to a neighbouring segment, and wherein
   neighbouring segments are provided with a tilting structure that forces neighbouring segments in a radial direction in relation to each other when the neighbouring segments slide axially in relation to each other
   wherein the tilting structure transforms relative axial movement of the neighboring segments to a radial movement of at least one of the neighboring segments and which tilting structure further comprises:
   a first element provided on a first neighbouring segment, and
   a second element provided on a second neighbouring segment, and
   which first element and second element engages when the neighbouring segments slide axially in relation to each other and wherein the first element and second element are shaped such that the neighbouring first and second segments are forced to move away from each other in a radial direction upon the engagement.

2. An injection apparatus according to claim 1, wherein the first and second elements comprise a tongue and groove.

3. An injection apparatus according to claim 2, wherein the tongue and the groove have sloping walls.

4. An injection apparatus according to claim 2, wherein each of the neighboring segments carries at least one tongue and one groove.

5. An injection apparatus according to claim 1, wherein the neighboring segments are provided with an engagement structure.

6. An injection apparatus according to claim 5, wherein the engagement structure allows axial movement of the neighboring segments in relation to each other.

7. An injection apparatus according to claim 5, wherein the engagement structure in the first neighboring segment is formed as a longitudinal groove and the engagement structure in the second neighboring segment is formed as a tail engaging the groove of the first neighboring segment.

8. An injection apparatus according to claim 1, wherein the housing is provided with a guiding structure for guiding the shield.

9. An injection apparatus according to claim 8, wherein the guiding structure is formed as a number of ribs.

10. An injection apparatus according to claim 9, wherein neighboring segments abut the ribs when the tilting structure are activated.

11. An injection apparatus according to claim 1, wherein the injection apparatus carries a cleaning chamber.

12. An injection apparatus according to claim 1 wherein the injection apparatus is a needle assembly attachable to an injection device.

13. An injection apparatus according to claim 1, wherein the injection apparatus is a handheld injection device.

* * * * *